(12) United States Patent
Burger et al.

(10) Patent No.: US 11,948,668 B2
(45) Date of Patent: Apr. 2, 2024

(54) INDIVIDUALIZED HEALTH PLATFORMS

(71) Applicant: Prosumer Health Inc., Hartford, CT (US)

(72) Inventors: Charles Burger, Brewer, ME (US); Don Holmes, Plano, TX (US); Gordon Jardin, Burlington (CA); Andrea Borondy Kitts, Glastonbury, CT (US); George Reigeluth, Hartford, CT (US)

(73) Assignee: Prosumer Health Inc., Hartford, CT (US)

( * ) Notice: Subject to any disclaimer, the term of this patent is extended or adjusted under 35 U.S.C. 154(b) by 0 days.

(21) Appl. No.: 16/398,448

(22) Filed: Apr. 30, 2019

(65) Prior Publication Data

US 2019/0333614 A1 Oct. 31, 2019

Related U.S. Application Data

(60) Provisional application No. 62/664,926, filed on Apr. 30, 2018.

(51) Int. Cl.
*G16H 10/60* (2018.01)
*A61B 5/00* (2006.01)
(Continued)

(52) U.S. Cl.
CPC ............ *G16H 10/60* (2018.01); *G16H 10/20* (2018.01); *G16H 80/00* (2018.01); *A61B 5/0022* (2013.01);
(Continued)

(58) Field of Classification Search
CPC ........ G16H 10/60; G16H 10/20; G16H 80/00; G16H 20/30; G16H 50/30; G16H 20/70; A61B 5/0022
(Continued)

(56) References Cited

U.S. PATENT DOCUMENTS 8,090,590 B2  1/2012 Fotsch et al.
9,886,594 B1  2/2018 Chaganti et al.
(Continued)

OTHER PUBLICATIONS

Schooley, Benjamin et al. "Patient-provider communications in outpatient clinic settings: a clinic-based evaluation of mobile device and multimedia mediated communications for patient education." JMIR mHealth and uHealth vol. 3,1 e2. Jan. 12, 2015, doi:10.2196/mhealth.3732 (Year: 2015).*
(Continued)

*Primary Examiner* — Christopher L Gilligan
*Assistant Examiner* — Bennett Stephen Erickson
(74) *Attorney, Agent, or Firm* — Ziegler IP Law Group, LLC

(57) ABSTRACT

A method of providing a user with an individualized health platform, includes collecting a user's health and care data, organizing the collected health and care data into a problem oriented health record, drafting health goals and a care plan for the user with the aid of a health coach, vetting the health goals and care plan using a data and analytics system to assure that the health goals and care plan are supported by peer reviewed health and clinical literature, producing individualized guidance options for addressing new acute or chronic issues, managing existing health issues, achieving the health goals, and adhering to the care plan based on the user's problem oriented health record, monitoring the user's achievements with respect to the user's health goals and adherence to the care plan, and providing additional guidance options based on the user's new health and care issues and the user's achievements and adherence.

12 Claims, 9 Drawing Sheets

(51) Int. Cl.
*G16H 10/20* (2018.01)
*G16H 20/30* (2018.01)
*G16H 20/70* (2018.01)
*G16H 50/30* (2018.01)
*G16H 80/00* (2018.01)

(52) U.S. Cl.
CPC ............. *G16H 20/30* (2018.01); *G16H 20/70* (2018.01); *G16H 50/30* (2018.01)

(58) Field of Classification Search
USPC ........................................................... 705/3
See application file for complete search history.

(56) References Cited

U.S. PATENT DOCUMENTS

| | | | | |
|---|---|---|---|---|
| 10,825,567 | B1* | 11/2020 | Wala | G16H 10/60 |
| 2008/0201280 | A1* | 8/2008 | Martin | G06N 20/00 |
| | | | | 706/45 |
| 2014/0156645 | A1* | 6/2014 | Brust | G06F 3/0481 |
| | | | | 707/722 |
| 2016/0012194 | A1* | 1/2016 | Prakash | G16H 40/40 |
| | | | | 705/2 |
| 2016/0071432 | A1* | 3/2016 | Kurowski | G16H 20/30 |
| | | | | 434/236 |
| 2016/0081575 | A1* | 3/2016 | Wu | A63F 13/332 |
| | | | | 600/301 |
| 2018/0000347 | A1* | 1/2018 | Perez | A61N 1/36014 |

OTHER PUBLICATIONS

Hsu et al., "Utilization of a Cloud-Based Diabetes Management Program for Insulin Initiation and Titration Enbles Collaborative Decision Making Between Healthcare Providers and Patients," Diabetes Technology & Therapeutics, vol. 18, No. 2, 2016.

Islam et al. "Recent Advancement of Clinical Information Systems: Opportunities and Challenges," Yearbook of Medical Informatics, Aug. 2018.

* cited by examiner

INDIVIDUALIZED HEALTH PLATFORMS

RELATED APPLICATIONS

This application claims the benefit of U.S. Provisional Application No. 62/664,926, filed on 30 Apr. 2018, the contents of which are incorporated by reference in their entirety.

FIELD

The disclosed exemplary embodiments are directed to a health management system, and in particular, to a dynamic, learning, individualized health and care management system that is customized, or individualized, specifically for each participating individual.

BACKGROUND

There have been difficulties in delivering health and care efficiently and at a reasonable cost. The present uncoordinated, poorly integrated health and care efforts are inaccessible, complex, expensive, inefficient, and error prone.

The year after year deterioration of health outcomes across the board—e.g. overall mortality, maternal and infant mortality, rising rates of a growing list of chronic diseases, that are poorly managed, growing rates of mental disorders and a substance abuse epidemic—lead to less than desirable outcomes for millions each day. Improving the health of the population is supposed to be what the whole public health and healthcare endeavor is all about. Instead, there has been a steady decline of the most important measures of the health of the population compared to itself over time and to other developed countries.

For many years the mental health and substance abuse situation has been getting worse and worse. The recent outbreak of the opioid addiction epidemic is only the worst manifestation of this long festering set of problems.

Of particular note is that of all the professions, healthcare professionals have the highest rates of mental health issues, substance abuse and suicide.

For decades the decline of the physical condition of the public health infrastructure has been well documented—e.g. the underinvestment in basic maintenance has led to a deterioration of public water systems, solid waste disposal systems and other systems.

There are many without access to basic healthcare insurance, millions more who are under-insured, who have the wrong kind of insurance and/or who must pay such high deductibles that they are unable to use the insurance they do have and thus do not see clinicians when they should for acute, chronic and/or preventive care.

For multiple reasons, there has been a growing shortage of physicians and nurses, making it difficult for those who do have insurance to get access to care, particularly at the primary care level and especially for low income people.

Even for those who do have insurance and can get access to care, the quality and safety of that care has been declining for years leading to higher and higher rates of iatrogenesis—preventable medical mistakes, which have for some time been the third highest cause of death. In 2015, 440,000 people died of preventable medical mistakes in the hospital setting alone. This figure does not include deaths in other settings, such as primary care, other ambulatory care, home care, etc. Nor does it include the number of people who are injured, but not killed, by medical mistakes. Worst of all, there is no system for tracking, measuring and diagnosing the root causes of these errors, making it difficult to determine the size of the problem.

It is very difficult for an individual to have a basic understanding of costs, prices, who pays for what, why and for what reasons. As a result, it is not possible to inject market discipline and the efficiencies of typical market mechanisms into healthcare because normal dynamic market data about changing supply and demand and resulting prices do not exist.

Most reimbursements are still done based on the volume of care provided, not on the value or quality and cost of the care delivered.

The ability to pay for and provide decent long-term care for the growing millions of elderly people whose life spans continue to increase year after year is a part of the health, care and cost crisis that no one wants to talk about. The result is that the overwhelming burden of long-term care falls on family members and/or poorly paid home healthcare workers many of whom have no political power or representation.

Healthcare costs are at an all-time high with unfavorable health outcomes. It is estimated that about a third of the costs are wasted on unnecessary care, delays, errors, corruption, administrative complexity and general inefficiencies.

An individual may be under the care of several different heath care providers, each of which may request that the individual provide a health and care history, typically by filling out a form. However, the individual may not know or remember all the details of their health and care history, and the form may not be detailed enough and most likely will not be customized to capture pertinent data that may be specific for that particular individual. Furthermore, in most cases, an individual's health and care records are not stored together and are typically scattered among the individual's various health care providers. Even when an individual's health and care records are stored together, the records are usually organized in vertical stacks by record type, such as laboratory results, images, medications, tests performed, etc., which makes it difficult to understand relationships among the records and any health problems and treatments an individual may have experienced, or is presently experiencing.

It would be advantageous to provide a dynamic, learning, individualized health platform that addresses these shortcomings and others of the health and care situation.

SUMMARY

The disclosed embodiments are directed to individualized health platforms (IHPs) that operate to organize, integrate, and coordinate, care and health around each user's whole body and mind. Each human body is a system of interdependent biological organ systems. What goes on in one system effects what goes on in the other systems. To deliver optimum care and health promotion, it would be advantageous to approach each new health and care encounter in a holistic manner, considering all aspects of the health and care previously and presently being administered to every part of an individual user in the context of the relevant peer reviewed health/clinical literature.

The disclosed embodiments allow a user to have 24/7 access to their IHP that, when considering a problem, weighs all aspects of the user's previously experienced health and care actions and experiences when proposing guidance options for share decision making between the user of the IHP and their health coach and other members of their care team, that is, anyone who may participate in the health care of the user. A user may utilize various health monitoring devices, for example, portable, digital home monitoring devices, to monitor many different physiological processes—e.g. blood glucose, INR, blood pressure, temperature, heart rate, breathing rate, etc., and the disclosed embodiments may provide the user with the ability to vet and then input the information from these devices into a user terminal for entry into the user's individualized personal health record, organized in a manner that provides a view of the user's health as a whole. In other embodiments, an interface may be provided that may directly collect the information from these devices and provide the collected information to the user's IHP.

Machine and software-based, semi-automated health/ clinical content development processes and systems with natural language processing and semantic parsing technologies may be utilized to read, parse and extract data from voluminous numbers of peer reviewed journal articles, text books, survey reviews for keeping the IHPs up-to-date with the most recent health and clinical research findings, data and guidance on best practices.

The disclosed embodiments may employ artificial intelligence to analyze new data on a user's changing health in the context of all the other data in that user's health record and in the context of the relevant health/medical literature to produce refinement questions on the initial data on a new chronic/acute problem, and thus provide individualized guidance options, documentation about what is going on, recognition of patterns in the data, continuous system learning based on the flow of new data, identification of best practices for that individual and better health, care, and cost outcomes and findings.

Behavioral psychology, specifically behavioral economics, may be employed to provide insights into how decisions are made and how to shape and change individual behavior. Advances in the data, decision, learning and cognitive sciences may contribute to promoting understanding the nature and limits of human decision making, cognitive biases in making those decisions, and how all these factors interact to effect individual behavior.

New care and health models may provide new insights into how these advances in other domains can be brought to bear in health and care to help users of the IHPs become more engaged in their care and health—e.g. a Continuous, Collaborative Care Model reflects the reality that care and health are continuous endeavors which often require collaborative efforts of multiple people in an ongoing manner.

It is clear that a new system and paradigm are required that work from the bottom up—one user at a time—and whose whole purpose and mission is devoted to helping each user optimize their health and healthcare, as opposed to the financial interests of payers and providers. Users utilizing the disclosed embodiments may address more of their own health and care issues themselves with the help of the present system, thus becoming both providers and consumers—or the new "prosumers"—of their own health and care efforts.

The disclosed embodiments are directed to a method of providing a user with a dynamic, learning, integrated individualized health platform, including collecting a user's health and care data, organizing the collected health and care data into a problem oriented health record, drafting health goals and a care plan for the user with the aid of a health coach, and using the peer reviewed health and clinical content to vet the user's draft goals and plans to ensure that they follow best medical practices from that content. Users may then use their IHPs to address new acute or chronic health and care issues by responding to refinement questions coming from the literature about the new issue. The user's answers to those questions are then analyzed by an AI analytics engine in the context of all of the data in that user's problem oriented health record and in the context of the relevant peer reviewed literature to produce near real time guidance options for shared decision making by the user, their health coach and other members of the user's care team.

The method may include vetting the health goals and care plan using a data and analytics system that operates to assure that the health goals and care plan are supported by applicable peer reviewed health and clinical literature, producing individualized guidance options for achieving the health goals and adhering to the care plan based on the user's problem oriented health record, monitoring the user's achievements with respect to the health goals and adherence to the care plan, and providing additional guidance options based on the user's achievements and adherence.

Collecting the user's health and care data may include collecting data from one or more electronic medical records and user health monitoring devices.

Collecting the user's health and care data may include determining the user's individual social and environmental health determinants.

Organizing the collected health and care data into a problem oriented health record may include organizing the collected health and care data chronologically according to diagnostic, treatment and management guidance, and processes used to address particular medical issues.

Organizing the collected health and care data into a problem oriented health record may include organizing data relating to a particular health and care issue as a series of micro-care encounters arranged in chronological order.

Vetting new data coming into the user's health platform or vetting the health goals and care plan may include using the data and analytics system to analyze peer reviewed health and clinical literature to produce health and clinical analytics and individual health and care knowledge elements, establish standards for quality of the data inputs and the peer reviewed health and clinical literature, and vet the health goals and care plan by comparing the health goals and care plan to the data in the peer reviewed health and clinical literature.

The method may further include vetting the set of determined health goals and care plan by a user's physician.

Monitoring the user's achievement of the health goals and the user's adherence to the care plan may include working with the health coach to carryout health activities for achieving the user's health goals and care plan.

Monitoring the user's achievement of the health goals and the user's adherence to the care plan may include inputting data indicating by the user when a care plan activity is complete, and using the data and AI analytics engine to analyze the user's input against the guidance options, shared decision making and the health goals and care plan.

Providing additional guidance options may include using the data and AI analytics engine to analyze the user's data inputs in the context of all of the data in the user's problem oriented health record and in the context of the applicable peer reviewed health and clinical literature to produce ongoing guidance options in response to new acute and chronic issues for the user to discuss in shared decision making with the health coach.

The method may further include receiving additional data from the user, and using the data and analytics system to analyze the additional data and identify a potential health problem, present the user with one or more of a set of refinement questions about the potential health problem from the peer reviewed literature, or a screening survey for the potential health problem, wherein the screening survey poses refinement and qualifying questions derived from the peer reviewed health and clinical literature applicable to the potential health problem, perform an analysis of the answers to the refinement questions in the context of the data in the user's problem oriented health record, individual social and environmental health determinants, and in the context of the peer reviewed health and clinical literature related to the new health problem to determine further individualized guidance options for shared decision making.

The method may further include using the further individualized guidance options in shared decision making to plan further health and care steps for resolving the health care problem.

The method may further include storing the individualized guidance options, the health goals and care plan, data related to the user's progress towards the health goals and the user's adherence of the care plan, the additional guidance options resulting from the shared decision making, the further individualized guidance options, and further health and care steps in the user's problem oriented health record.

The health coach may communicate with the user to ensure that the user carries out the health and care activities agreed to as a result of the guidance options and the shared decision making and discussions.

The method may further include providing the user with access to their problem oriented health record at all times.

The following sections describe the unique components of the system providing the individualized health platforms, how each of the components works and how the overall system works, how a hypothetical user may use the system to address different care and health issues, and the benefits of the system.

DETAILED DESCRIPTION

The aspects and advantages of the exemplary embodiments will become apparent from the following detailed description considered in conjunction with the accompanying drawings. It is to be understood, however, that the drawings are designed solely for purposes of illustration and not as a definition of the limits of the invention, for which reference should be made to the appended claims. Additional aspects and advantages of the invention will be set forth in the description that follows, and in part will be obvious from the description, or may be learned by practice of the invention. Moreover, the aspects and advantages of the invention may be realized and obtained by means of the instrumentalities and combinations particularly pointed out in the appended claims.

Figure 1:
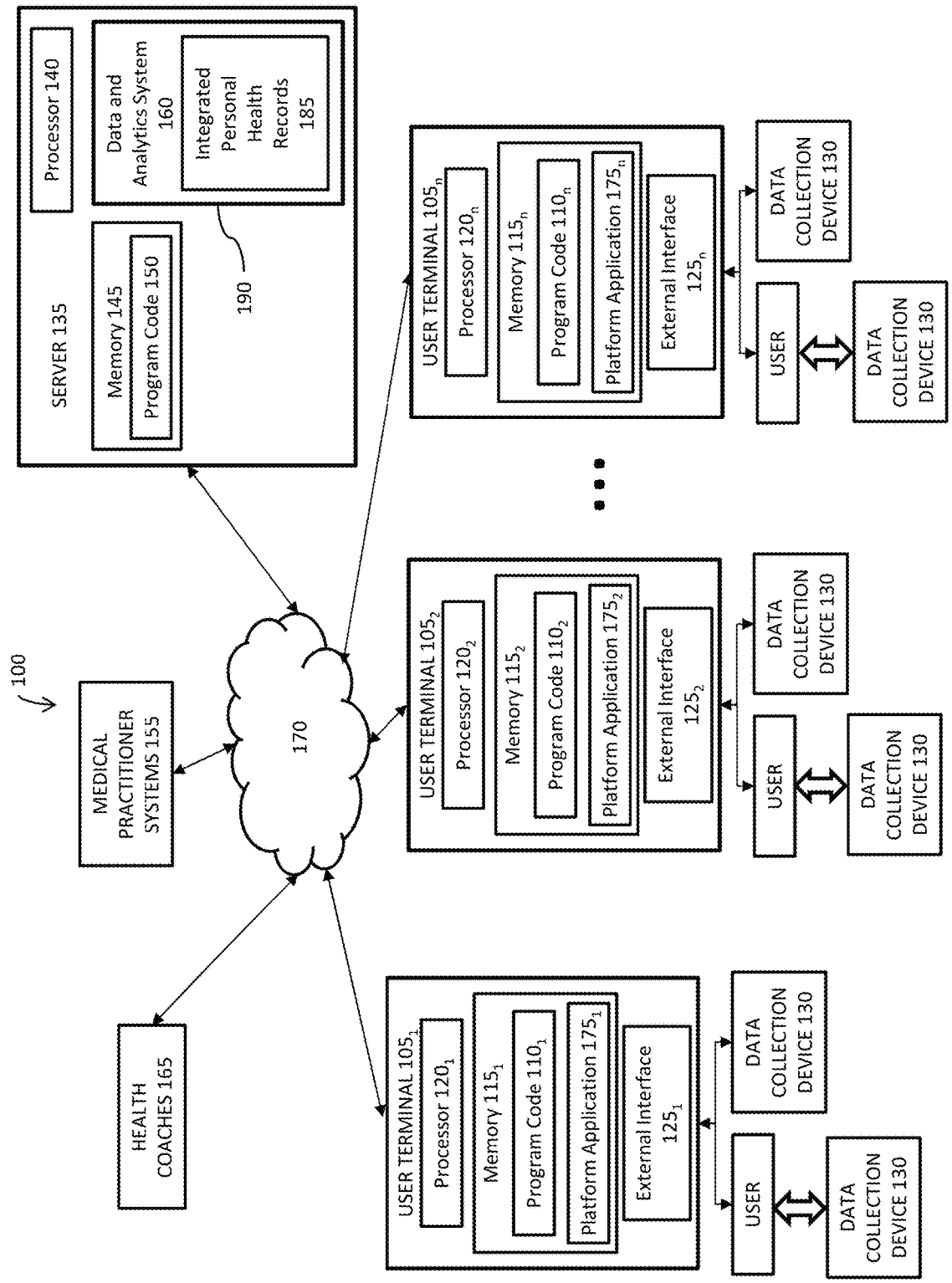
FIG. 1 shows a schematic illustration of an exemplary health management system according to the disclosed embodiments.

FIG. 1 shows a schematic illustration of an exemplary dynamic, learning, individualized health and care management system 100 that implements IHPs 190 according to the disclosed embodiments. The system may include one or more user terminals $105_1$-$105_n$. The user terminals $105_1$-$105_n$ may each operate a platform application $175_1$-$175_n$ that provides access to the IHPs 190, which may be located on the server 135.

For purposes of the disclosed embodiments, the IHPs 190 are implemented by a data and analytics system 160, that operates to organize users' health records 185 in an integrated fashion, and link vetted health and care knowledge fragments, health and clinical analytics, input from an assigned health coach 165, and the integrated users' personal health records 185, to provide ongoing, real time evidence-based individual healthcare guidance options.

Each user can access their own IHP 190 at anytime from anywhere through multiple digital devices, shown in FIG. 1 as user terminals $105_1$-$105_n$,—e.g. for example, a desktop computer, a laptop, a tablet, a mobile phone, or any other computing device capable of performing the functions of the disclosed embodiments. It should be understood that a user may utilize more than one computing device and more than one type of computing device to access the user's IHP 190. For example, a user may use a mobile phone at one point in time to access the system and later may use a tablet for system access. It should also be understood that a user terminal, with the proper permissions, may be shared by a user and their health coach, and/or other members of their care team, other users, may be carried by a user, and may be located at, for example, a user's residence, a medical practitioner's office, a hospital, or any suitable location with internet access.

Each user terminal $105_1$-$105_n$ may include computer readable program code $110_1$-$110_n$ stored on at least one non-transitory computer readable medium for carrying out and executing the processes described herein. In at least one embodiment, the computer readable program code $110_1$-$110_n$ may implement the platform application $175_1$-$175_n$ for providing, in combination with other components of the dynamic, learning, individualized health and care management system 100, access to the IHPs 190. The computer readable medium may be memories $115_1$-$115_n$, and in alternate aspects, the computer readable program code $110_1$-$110_n$ may be stored in memories external to, or remote from, user terminals $105_1$-$105_n$. Memories $115_1$-$115_n$ may include magnetic media, semiconductor media, optical or voice/audio media, or any media which is readable and executable by a computer. Each user terminal $105_1$-$105_n$ may also include a processor $120_1$-$120_n$ for executing the computer readable program code $110_1$-$110_n$.

Each user terminal $105_1$-$105_n$ may also include at least one external interface $125_1$-$125_n$. In at least one embodiment, the at least one external interface $125_1$-$125_n$ may include a keyboard, mouse, touch screen, display camera, microphone, voice recognition system, or any device or combination of devices suitable for providing a user with an ability to interact with the dynamic, learning, individualized health and care management system 100. In some embodiments, the at least one external interface $125_1$-$125_n$ may include a wireless interface, for example, Wi-Fi 802.11, Bluetooth 802.15, cellular 2G-5G, or any other suitable wireless interface. Some embodiments may also include a wired interface, for example, Ethernet, Universal Serial Bus (USB), Serial Advanced Technology Attachment (SATA) or any other suitable wired interface. The external interface may also provide a user with the ability to input health and care data for example, user perceived symptoms and data from data collection device 130, which may include for example, one or more medical monitoring devices, such as portable, digital home monitoring devices for monitoring various physiological processes—e.g. blood glucose, INR, blood pressure, temperature, heart rate, breathing rate, etc., environmental sensors, or any devices suitable for use as part of the dynamic, learning, individualized health and care management system 100. In some embodiments, the external interface 125 may directly connect to the one or more data collection devices 130 and may automatically collect the information from these devices, including an individual's favorite nutrition and/or fitness apps.

The health and care management system 100 may include one or more servers 135, each with a processor 140, and memory 145 storing computer program code 150 for generally operating the health and care management system 100 to provide the IHPs 190. The one or more servers 135 may be managed by a cloud computing services with suitable encryption and data security features and may include any commercially available cloud services. The server 135 may also include the data and analytics system 160 for analyzing data and literature. The data and analytics system 160 may also store integrated personal health records 185 for each user.

Each user may have a designated health coach 165 that may interact with a user when they want to communicate with a person about a health-related issue, for example, a chronic disease management issue, an emerging/existing acute problem, an insurance issue or an administrative issue. The health and care management system 100 health coaches 165 may receive training and may have certain qualifications and certifications. For example, the health coaches may have taken one of the recognized and approved Health Coaching accreditation and certification courses, successfully completed that course and received their certificate of completion. The health management system coaches 165 may operate to gain the confidence and trust of the users they work with through motivational approaches, empathy and compassion, and by following through on, and closing out each of the health and care tasks the health coaches 165 commit to perform for the users, and closing out each of the tasks the user commits to carrying out. If successful, a user will be able and want to become more involved in achieving their health goals and care plan in the manner that works best for them. To build up this confidence and trust may take time and lots of little steps and nudges, and each user will have different triggers for involvement, different strengths and weaknesses, different preferences and psychologies, families, chronic diseases and family and work situations. The health and care management system 100 gives the user and their health coach many opportunities to build this trust through the enrollment and planning processes that they perform together. In these many integrated and interdependent ways, the IHPs give the users the tools and the agency that they need to be able to take more personal responsibility for their own health and care and thus find their own path to improved health and care.

The various components of the health and care management system 100, including the user terminals $105_1$-$105_n$, one or more servers 135, medical practitioner systems 155, and one or more health coaches 165 may communicate over a network 170. In some aspects, the data collection devices 130 may communicate directly with the one or more servers 135 through the network 170.

Figure 2:
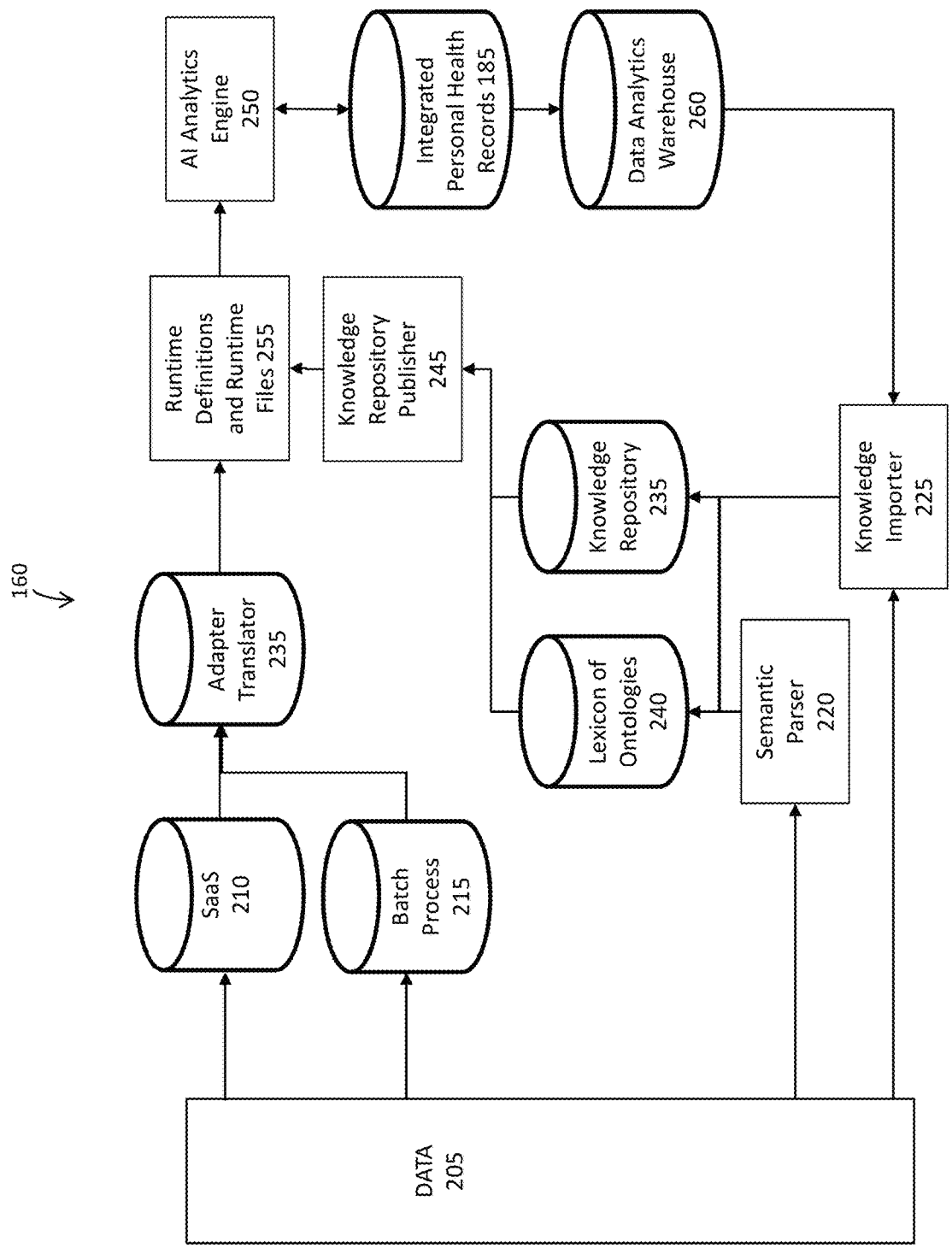
FIG. 2 shows a block diagram of a data and analytics system as utilized by the disclosed embodiments.

FIG. 2 shows a block diagram of the data and analytics system 160. The data and analytics system 160 generally provides:

Normalized knowledge concepts in a domain so that ideally a concept need only be described in one way, with one combination of data elements;

Efficient and accurate acquisition of health and medical knowledge content;

Similarity matching between language based external knowledge and language generated from a lexicon 210, so that matching of concepts is accurate and efficient;

Data storage through the lexicon 210 in a machine language, including language models that allow concepts and content to be rendered in natural language for interpretation and review;

The ability to gather multiple external data sets into one coherent data dictionary as well as support and integrate customer creation of new vocabularies as needed to support new domains;

Support for a wide range of relationships between normalized and de-normalized data elements (string synonym, weak synonym, strong antonym, weak antonym, etc.);

Manage and ensure continuity of data element changes including effects on decision engine rules or patterns and subsequent versions of included ontologies; and;

Support easy visualization of data relationships and uses.

The data and analytics system 160 generally houses the integrated personal health records 185 for each user and may include various facilities for automatically importing large volumes of health and clinical data 205 for use in analyzing all of a user's integrated health and care information and assessing diagnostic, treatment and management options. The various importing facilities may include, for example, a software as a service system 210, a batch processing system 215, a semantic parser 220, a knowledge importer 225, or any other system appropriate for importing particular types of data. In some embodiments, the software as a service system 210 and the batch processing system 215 may generally operate on data related to individual users, while the semantic parser 220 and knowledge importer 225 may generally operate on data related to populations.

The software as a service system 210 may be used to extract bulk data from medical monitoring devices, third party applications, web sites and other sources that may be conditioned using a software as a service application. The batch processing system 215 may typically process bulk data available in batch formats, such as EHR (Electronic Health Record), CODA (Consolidated Clinical Document Architecture), HL7 (Health Level-7), or any other format suitable for batch processing. The bulk data may then be vetted, curated, coded into a standard format, disaggregated, and associated with the particular integrated health record of an individual, by the adapter translator 230. The adapter translator 230 may also perform validity checks on the data, such as range limits for variables.

The semantic parser 220 may operate to parse vetted published works to produce representations in predicate logic or other formal language. The formal language may be stored in a knowledge repository 235 and may be further parsed for vocabulary for use in a lexicon of ontologies 240. The knowledge importer 225 may operate to analyze structured data sets, for example, data in Unified Medical Language System (UMLS), Systemized Nomenclature Of Medicine (SNOMED), or any other suitable format for use in the knowledge repository 235 and the lexicon 240. The semantic parser 220 and the knowledge importer 225 may also operate to vet, curate, code into a standard format, and provide validity checks on the imported data. A knowledge repository publisher 245 may operate to publish the contents of the knowledge repository 235 and the lexicon of ontologies 240.

The data and analytics system 160 may also include an artificial intelligence (AI) analytics engine 250 that may have machine learning and natural language processing functions. The AI analytics engine 250 may operate on the bulk data vetted and curated by the adapter translator 230, and the contents of the knowledge repository 235 and the lexicon of ontologies 240 published by the knowledge repository publisher 245, as runtime definitions and knowledge files 255, and may operate on the integrated personal health records 185 for each user, to generate and update the IHPs 190 as disclosed herein. The AI analytics engine 250 generally provides:

Pattern matching, including set intersection vs. non-intersection, identifying pattern match-based trigger patterns, nested patterns of rising complexity and patterns where combinations of elements provide weight greater than the sum of their individual parts, and pattern matches based on predictive patterns and data points;

A dual-sum calculation that reconciles positive and negative data into a ranking;

Set theory/relational algebra;

Use of a formal ontology or lexicon;

Neural classification, using layered heuristics that are evidence or science based;

Text mining;

Similarity matching;

Relational data modeling and normalization;

Space efficient, lossless data representation; and

Lossless data assessment.

The data and analytics system 160 may operate to review the large volumes of current peer reviewed health and clinical literature in the different health and clinical areas, as stored in the lexicon 240 and the knowledge repository 235, to produce health and clinical analytics and individual health and care knowledge elements that may be time stamped and coded. The health and clinical analytics and individual health and care knowledge elements may be analyzed by the AI analytics engine 250 to provide updated guidance options in response to data that may be introduced into a user's integrated personal health record 185 from electronic medical records, medical devices, sensors, etc. The studies may be vetted for quality, peer review, and timeliness by a panel of experts before being processed by the data and analytics system 160. The processed data may be coded in various ways, including according to a particular topic, such that related data, for example, data related to obesity, may be collected and the new data may be integrated with the individual's data to determine what is the health and care meaning of that new data in the context of all of the other data for that individual, and may be used in an analysis of issues which a user's IHP 190 may be currently addressing. As a result of the range limits for each data element, the vetting, coding, and integrating processes, the health and care management system establishes de-facto standards for the quality of the data and information processing used in analyzing the data. As a further result, each piece of guidance produced by a user's IHP 190 may be evidenced/best practice based, and users may be provided with a facility to view the reasoning and references behind each piece of guidance.

As a result, transparency may be maintained throughout each IHP 190 so that the reasoning and references from which each guidance was produced may be examined, and it may be demonstrated that the guidance options are based upon best practice evidence. The data and analytics system 160 may update the data periodically on an automatic basis by checking for new studies and literature and may also be programmed to update the data immediately if a new study comes out on a particular topic that has been identified as having particular significance for changing best practices for health and care.

The data and analytics system 160 may provide ongoing, real time evidence-based individual acute care and diagnostic, investigation, treatment and chronic disease management guidance—e.g. "What should I do next" and why, based on a combination of constantly updated medical literature sources and data in a user's integrated personal health record 185. A user's IHP 190 may assess each new piece of data about a new issue in the context of all the other data in that user's integrated personal health record 185 and in the context of the relevant medical evidence that may be developed by the data and AI analytics Returning to FIG. 1, the operation of the platform application 175, the data and analytics system 160, and the server 135 will be explained.

Figure 3:
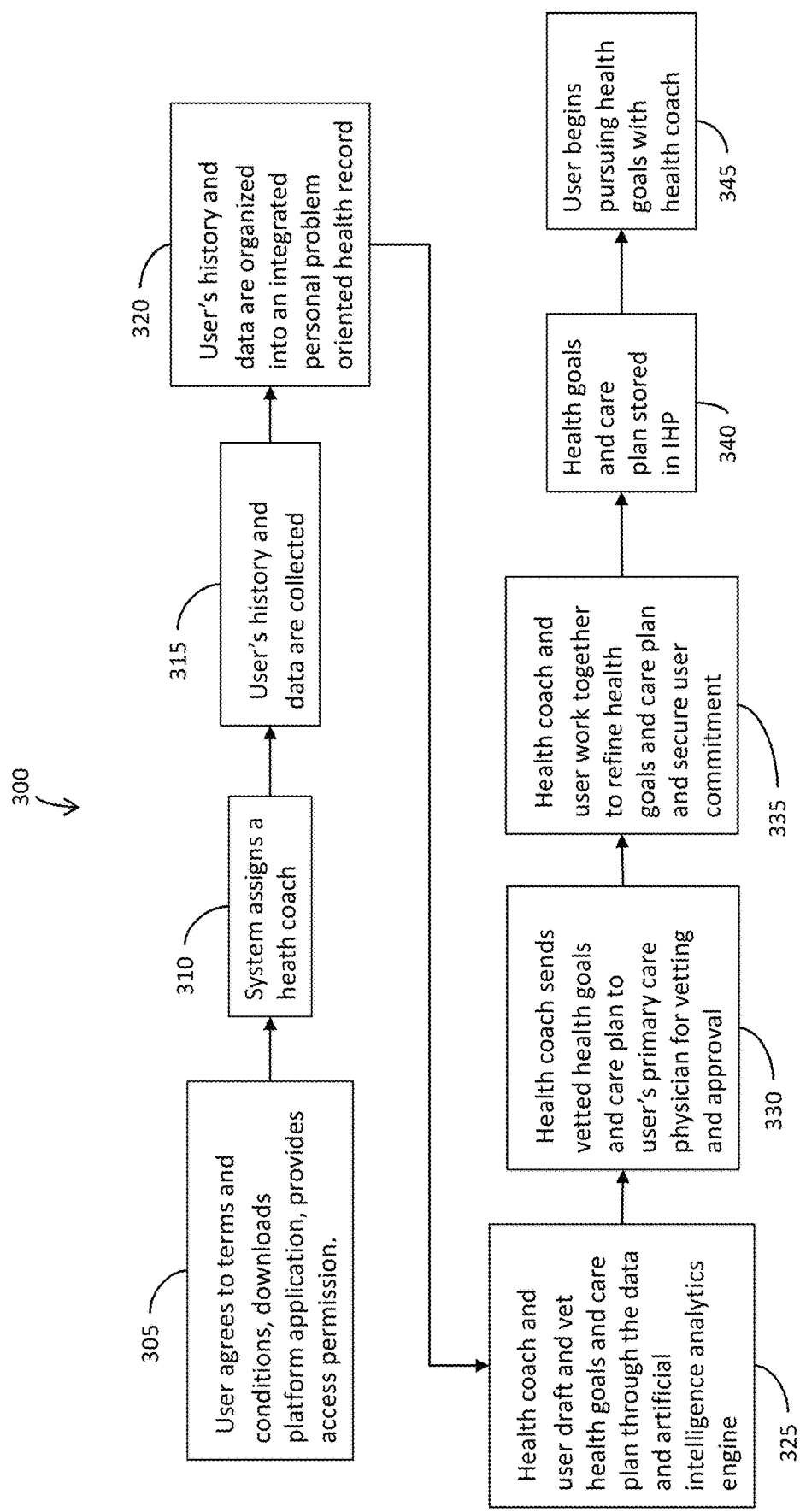
FIG. 3 shows a typical onboarding process for enrolling a user into the health management system.

The platform application 175 may provide users with the ability to enroll and to provide enrolled users with access to their IHPs 190. A typical onboarding process 300 for enrolling a user into the health and care management system 100 is shown in FIG. 3 and described below.

As shown in block 305, a user may decide to use the health and care management system 100, agree to the terms and conditions governing the use the health and care management system 100, download the platform application 175, and provide an assigned health coach, their physicians, and other members of their care team with access to their health and care data, as stored on the health and care management system 100. For example, the user may fill out HIPAA forms or may provide other forms of permission. The system may then assign the user a health coach, as shown in block 310.

The user's health and care history and data may then be collected as shown in block 315. The health coach may collect the user's health and care history and data during an in person interview, may send the user a list of health/care data items for the user to fill out and return, and the user's various other health care providers, or the other health care providers data systems, may be polled for the user's health and care data.

It should be noted that, in addition to the user's health and care history, the system, through questionnaires developed by one or more of the health coach 165, a primary care physician, or by the data and analytics system 160, may collect a list of individual social and environmental health determinants for use in developing the user's health and care plan, and in producing and assessing which guidance options make the most sense for a particular new health or care issue. Only about 10-20% of an individual's health status may be determined by what goes on in various clinical settings. The rest of a person's health status may be determined by the attitude, character, discipline, behavior and activities of that person, which are in turn influenced by their neighborhood, their personal security, their social support network, their education and income, the condition of their housing and many other similar variables or social determinants.

Not all a user's data must be collected during the enrollment process for the user to begin using their IHP 190. Instead, the user's data may be collected iteratively over time, to obtain a complete set of health and care data for a given user in their integrated personal health record 185. As shown in block 320, the integrated personal health records 185 may be collected from the user's input and from the user's various health care providers, and the data and analytics system 160 may organize the integrated personal health records 185 in a problem oriented manner. For example, for an individual diagnosed with arthritis, a record of the symptoms, a collection of x-rays, treatment procedures, medications prescribed during those procedures, surgery records, rehabilitation programs and other records may be organized together to provide a comprehensive medical history of the individual, organized according to problems experienced by the individual over time. In some embodiments, the records may be further organized in a time line, for example, in order of each step in the diagnostic and treatment and management process. As another example, all the data relating to a particular health and care issue may be displayed horizontally as a series of micro-care encounters (defined below) and may show each item or event that occurred during each micro-care encounter. These micro-care encounters may then be arranged chronologically to enable users of the data to get a picture of how that issue has been addressed over time.

Once the user's data has been collected, the health coach and user may draft health goals and care plan and vet the plan through the data and analytics system 160, as shown in block 325. Using the techniques and operations discussed above, the data and analytics system 160 may operate to compare the individual's health and care data against peer-reviewed health and medical literature recommended actions—e.g. if an African American woman is taking beta blockers for her hypertension, the data and analytics system 160 may provide guidance to suggest a calcium channel blocker because African American women do not respond as well to beta blockers as they do to calcium channel blockers. The data and analytics system 160 may be utilized in the same way for contra-indications—e.g. someone on warfarin should not take ibuprofen, etc.

As shown in block 330, the health coach may then send the vetted health goals and care plan to the user's primary care physician for review and approval. As shown in block 335, the user's primary care physician may vet and approve the health goals and care plan The health coach 165 and the user may work together to refine the user's health goals and have the user commit to the user's health goals and care plan, and as shown in block 340, the health goals and care plan may be stored in the user's IHP 190. The health coach 165 and user may begin implementing the agreed upon health and care plan, as shown in block 345.

Many of the user's health goals may be based on the user's health and care data—e.g. if the user has high blood pressure of 180/90, one of the user's health goals will be to reduce their blood pressure to let's say 140/90 within three months of working together. This health goal may differ from the population guideline of 120/90 because this individual may have other health traits that make a different blood pressure goal desirable and possible. In turn, much of a user's care plan may derive from their health goals—e.g. if one of the user's health goals is to reduce blood pressure from 180 to 140, and this user is an African-American female, then the care plan may stipulate that she take a calcium channel blocker to reduce her blood pressure, and not the usual recommendation of a beta blocker and/or an ACE inhibitor, because they don't work as well for African-Americans as calcium channel blockers. Once the user and the health coach 165 have put together the draft health goals and care plan, the data and analytics system 160 and the user's primary care physician may check them for accuracy, internal integrity, contra-indications and completeness. The user and the health coach 165 may then commit to carryout and achieve the health goals and the care plan by using the user's IHP 190 on a daily basis if necessary and in a way that works best for the particular user.

Health goals may be determined through a combination of the health data for a given user—e.g. if they have high blood pressure, they will have as one of their health goals to reduce their blood pressure—and personal preferences—e.g. person is not obese or overweight, but wants to lose ten pounds, etc. Health goals may be prioritized by severity/acuity indexes developed by the data and analytics system 160 when analyzing the medical data 205, —e.g. blood pressure of 200/120 with a headache may be a malignant headache emergency and may have a higher priority than the person's blood glucose reading of 150, which is a health goal but may not be triaged as quickly as the malignant headache.

In some embodiments, the user's integrated personal health record 185 may be stored on the server 135 and may be managed by a cloud computing provider with suitable encryption and data security features. The overall architecture of the IHPs 190 may provide further security for the user's data by storing the user's personal identifier data on the user's user terminal 105 and storing the user's health and clinical data on the cloud-based server with a coded reference key linking the two sets of data. Each user's integrated personal health record 185 may be implemented as an integrated health and care data base that may include all an individual's providers, health insurance details, medical history and problems, including problem list, dental and eye care and mental health, vital signs, history, nutrition, exercise, allergies, medications, blood type, etc. integrated in one record, securely accessible by multiple heath care professionals across the care continuum—e.g. wellness, prevention, early detection, chronic disease management and acute care episodes. By having all an individual's health and care data in one integrated personal health record 185, the health and care management system 100 may ensure that every time a user has a new care/health issue the IHP 190 may assess that issue in the context of all that person's data—not just part of it as is the case today—and in the context of the relevant health/medical literature. Each piece of data may be time and date stamped and coded in such a way that all the data that relates to a particular subject, such as diabetes type 2, can be assembled and analyzed together.

Figure 4A:
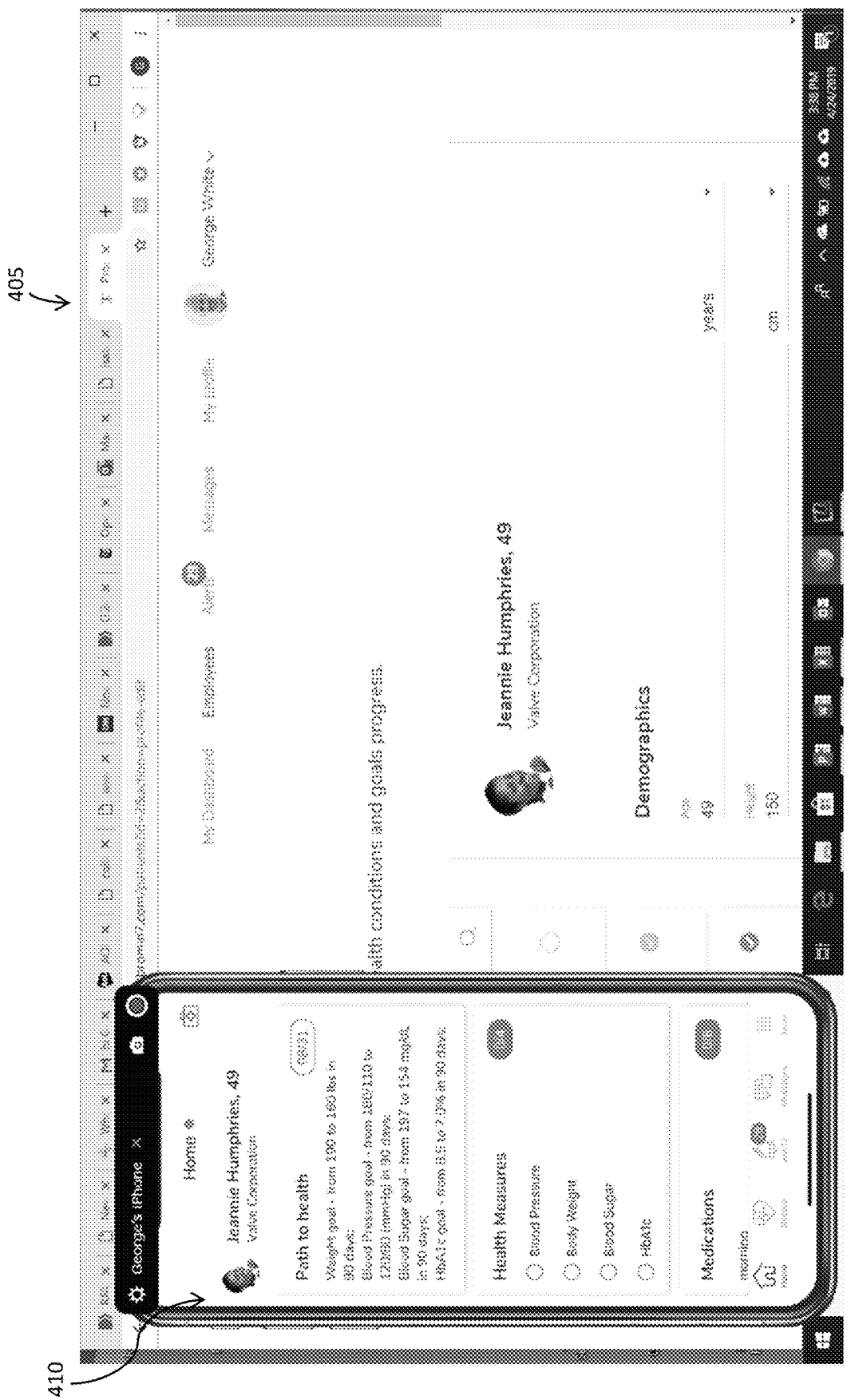
FIG. 4A shows an example of an intake form and a screen shot of an exemplary app for the enrolling process and ongoing utilization of the exemplary health management system.
Figures 4B, 4C:
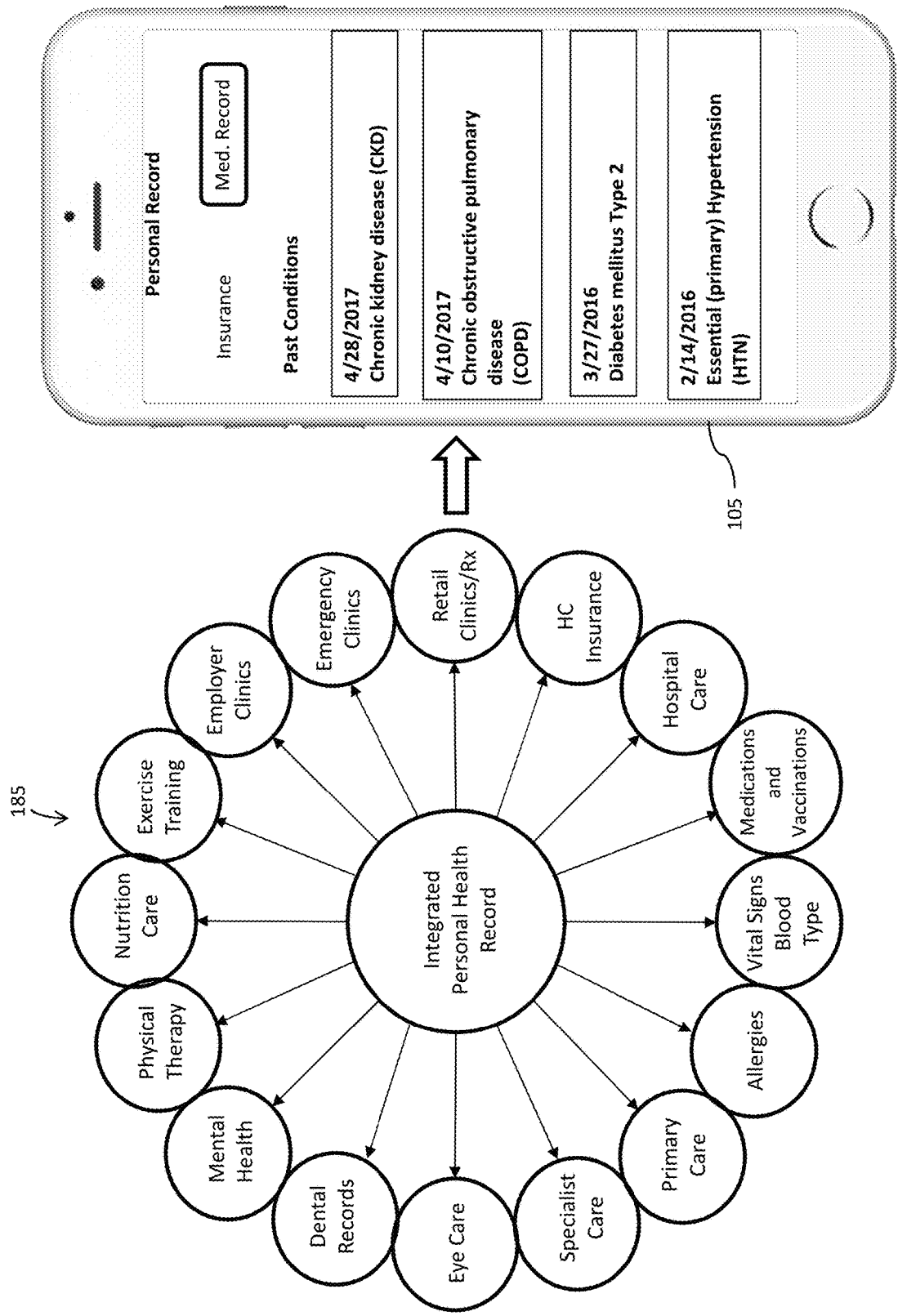
FIG. 4B shows an example of the types of medical records that may be included in an integrated personal health record.
FIG. 4C illustrates how previous problems may be displayed on a user terminal 105.

FIG. 4A shows an example of an intake form 405 and a screen shot of an exemplary app 410 for the enrolling process and ongoing utilization of the exemplary health management system. FIG. 4B shows an example of the types of medical records that may be included in an integrated personal health record 185, and FIG. 4C illustrates how previous problems stored in the IHP may be displayed on a user terminal 105. The user's integrated personal health record 185 may include the user's individual social health determinants, mentioned above, which the health coach 165 and the user may consider when drafting the health goals and care plan, and the data and analytics system 160 and primary care physician may utilize when vetting the health goals and care plan. For example, if someone has asthma, one of their health goals might be to reduce the number of asthma exacerbations. One of the determinants of asthma exacerbations may be mold in an individual's house. Another determinant may be neighborhood ambient air quality. These determinants may be identified by the system as candidate causes of the user's high rate of asthma exacerbations, and the user and the health coach may work to reduce their severity and reduce the user's exposure to these risk factors.

The health and care management system 100 thus operates to include a wide range of possible environmental and social determinants of an individual's health. Recent studies have shown that healthcare provided in clinics presently may only account for about 10% of an individual's health status, even though it may account for about 90% of the total cost of an individual's health expenditures. Through this model, the individual and the health coach learn from their experience with each other and from the results of the data review performed by the data and analytics system 160, which determinants of health may be more important to a given individual. For example, while population level protocols and guidelines change frequently for health indicators such as cholesterol, blood pressure, lipid levels, etc., often the important thing for the individual is what level of a particular health indicator works best for them in terms of their own health situation, health and care goals and plans—e.g. it may be that for some people a blood pressure goal of 140—instead of the 120 population guideline—is more appropriate. These insights also help to drive more robust engagement by the individual in their care and health. While there is much talk about standardizing care, this is inimical to the reality that each of us has a different body with different health and care needs. Thus, the system may operate to standardize the quality of inputs so that the system can individualize, rather than standardize, care using a combination of the user's health and care history, and the user's individual social and environmental health determinants and the relevant health/medical literature.

Figure 5:
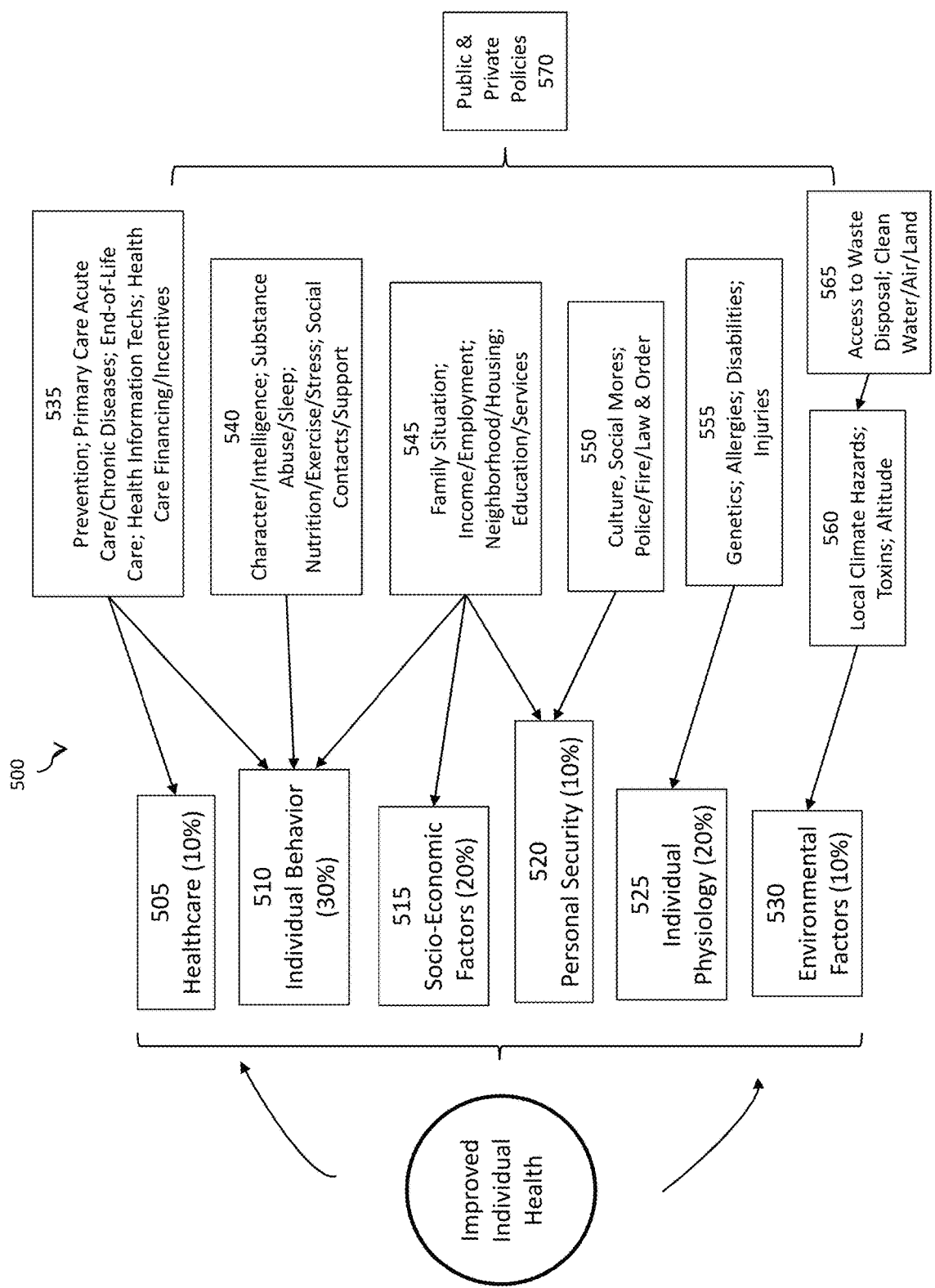
FIG. 5 shows an exemplary illustration of the individual and social determinants of individual health model.

An exemplary illustration of individual social and environmental health determinants that may be implemented in a user' IHP are shown in FIG. 5. The individual social and environmental health determinants 500 may be organized into a main set of factors, for example, healthcare 505, individual behavior 510, socio-economic factors 515, personal security issues 525, and environmental factors 530. Each of the main set of factors may have a number of driving characteristics, 535, 540, 545, 550, 555, 560, 565, that may in turn result from public and private policies 570.

Figure 6:
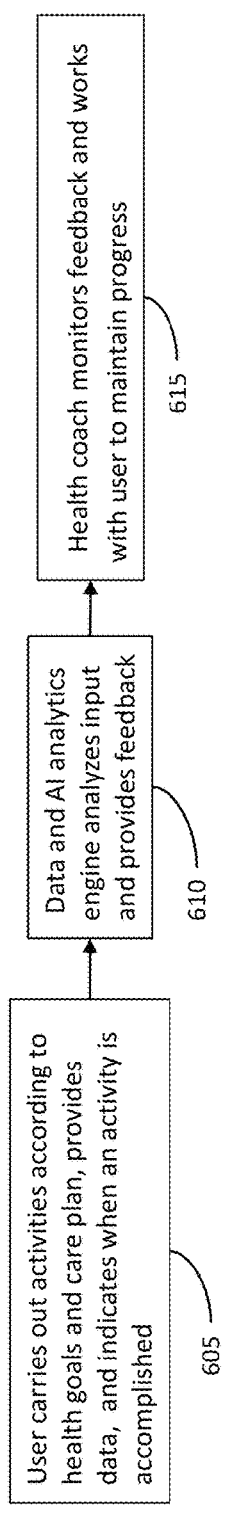
FIG. 6 illustrates feedback that may be provided to a user by a data and analytics system and a health coach.

Turning to FIG. 6, once the health goals and care plan are set, the user may proceed to carry out their daily health activities—e.g. health measures, medication, nutrition and fitness activities, and may use a user terminal 105 to input readings and other data and to indicate when a particular activity is done, as shown in block 605. The data and analytics system 160 may analyze the user's input against the stored health goals and care plan, and may provide feedback, as shown in block 610. For example, the data and analytics system 160 may send the user progress reports of how well the user is doing versus their health goals. The health coach may monitor each activity and may assist the user in maintaining their goals, as shown in block 615. For example, the health coach may remind the user when they have not done a particular activity, may congratulate them on their progress toward achieving their health goals, and may discuss issues the user is having with carrying out particular health activity.

Figure 7:
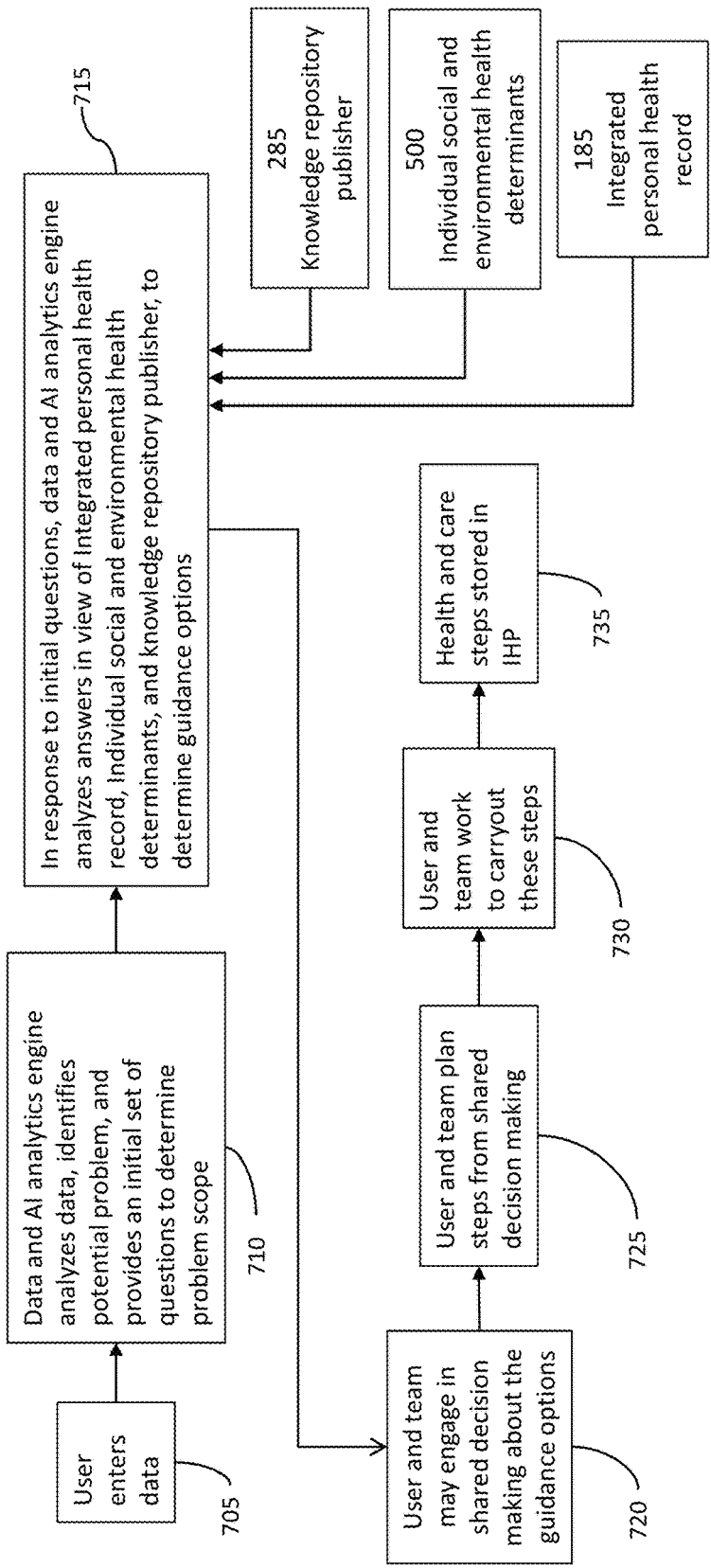
FIG. 7 illustrates that the data and analytics system may operate to identify a particular health problem from new data entered by a user.

As shown in FIG. 7, the data and analytics system 160 may also operate to identify a particular health problem from new data entered by a user. As shown in block 705, a user may enter data, for example, while following previously determined health goals, or as a result of identifying a potential health problem. As shown in block 710, the data and analytics system 160 may analyze the data, may identify a potential problem and may present the user with a screening survey for the potential health problem. The screening survey may pose refinement and qualifying questions from the medical literature about the possible health problem. As shown in block 715, the answers may provide an individualized, more precise and thus more accurate description of the user's condition. The data and analytics system 160 may then perform an analysis in view of the user's integrated personal health record 185, individual social and environmental health determinants 500, and information in the knowledge repository publisher 285, to determine individualized guidance options. As shown in block 720, the user and team may engage in shared decision making about the guidance options, and as shown in block 725, the user and team may plan steps resulting from the shared decision making. The user and team may then work to carry out these steps, as shown in block 730, and as shown in block 735, health and care steps may be stored in the user's IHP as part of the ongoing documentation, tracking and reporting of what goes on in each IHP.

As discussed below, all this activity with the health coach, the data, analysis, questions and answers, etc. may be documented by the system's documentation system so that users, providers and payers can easily see who did what, when, why the guidance provided for a particular micro-health encounter was produced, based on which questions and on which studies.

It should be noted that the integrated personal health records 185 for each user may be continuously updated with longitudinal data files of the individual user's health and care experience. The resulting knowledge accumulated regarding the individual user's successful health and care experiences, the bulk data vetted and curated by the adapter translator 230, and the contents of the knowledge repository 235 and the lexicon of ontologies 240 published by the knowledge repository publisher 245, may be utilized by the AI analytics engine 250 to generate and update a data analytics warehouse 260, which in turn may be fed back through the knowledge importer 225 to the knowledge repository 235. The updated data analytics warehouse information for each individual user may be used to further fine tune treatment options for each individual user. In machine learning terms, every data item stored in the system may be considered every time against every result known to the system in order to ensure maximum fidelity.

Thus, the individualized health platforms provide a new model of care and health in which N=1 that shows, through the longitudinal experience of each user, what works best for that user, as opposed to a population-based model of care. The health and care management system 100 may provide a continuous collaborative care model which implements an individual approach for contact between the individual and the coach—e.g. some users may want and need to be in communication, for example, through texting, emails, phone calls, as much as once a day or more to keep on track with respect to their care plans and health goals, medications, fitness, nutrition and other health activities. Other users may require less frequent contact. The continuous collaborative care model may encourage enhanced participation by individuals in their care and health because it reflects more accurately the way health and care needs express themselves in real life—e.g. differently for each individual and sometimes at unexpected moments—rather than the way care is currently provided through set episodes with a clinician in a bricks and mortar clinic. Prevention of chronic diseases and their effective management may require more continuous attention and pursuit of health goals and care plans than the current episodic care models permit. The continuous collaborative care model may begin with the collection of each user's health and care data from which the user, the health coach 165, the data and analytics system 160 and the user's primary care physician put together the user's health goals and care plans—e.g. if the user's data shows that the user has high blood pressure, one of the user's health goals will be to lower their too high blood pressure, and the care plan will make recommendations as to the best way to go about achieving that specific health goal—e.g. perhaps through a combination of daily monitoring of blood pressure with a home blood pressure monitor, better nutrition, more fitness activities and a medication program. The health coach 165 and the data and analytics system 160 as informed by the best peer reviewed literature will provide guidance options about possible nutrition, fitness and medication plans for specific health goals and related care plans. In working with the user and that user's IHP 190 to implement the continuous collaborative care model, the health coach 165 may use data guidance options and motivational techniques that each health coach 165 has been taught in their certification program to help the user find the best way to implement this model and thus achieve their health goals by adhering to their related care plan.

A micro-care encounter may be defined as a unit of measure or analysis that may be performed by a user, the health coach 165, a user's physician, or the data and analytics system 160—e.g. it could be the user taking their daily blood glucose level and entering that measure into their user terminal 105; or it could be the health coach 165 seeing that value and texting the user to say that compared to the last six days this latest blood glucose level is headed in the wrong direction; or it could be the data and analytics system 160 sending a user who has diabetes a hyperglycemia screening survey questionnaire; or it could be the user clicking on abdominal pain from the list of 25 acute symptom complexes to indicate that there is a problem and receiving back a list of refinement questions on abdominal pain from the literature. There are literally thousands of possible micro-care encounters. The important point here is that the user can respond right away to an issue that a micro-care encounter flags up—e.g. your latest blood pressure reading is headed in the wrong direction. Because there are in effect, three new providers, the user, the health coach 165, and the IHP 190, the use of traditional healthcare services may be reduced by the activities of these three new providers and the incremental cost of subsequent micro-care encounters may be significantly and progressively reduced.

Figure 8:
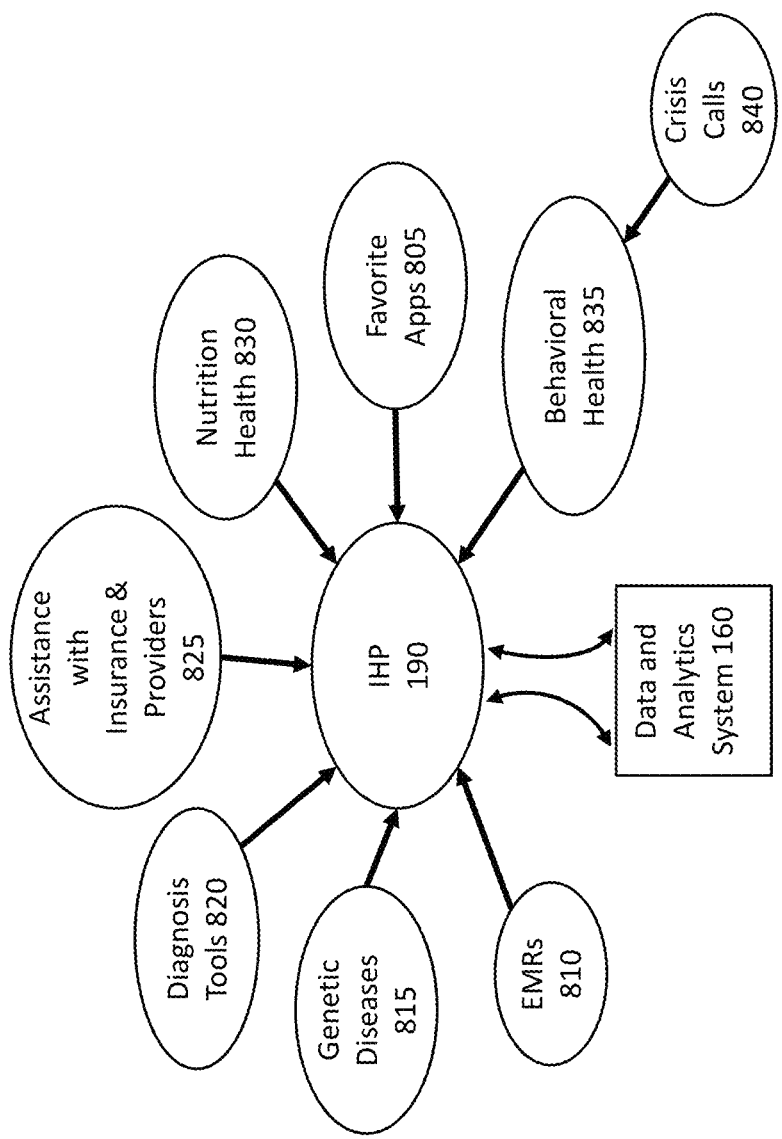
FIG. 8 illustrates how, because of a granular health/care data dictionary, language, architecture, etc. each user can connect external databases to their individualized health platform and adapt the structure and content of the underlying data architecture in response to new developments—e.g. personal genome, metabolome, other—omic data, cost data, etc.

FIG. 8 illustrates that each user can connect external information and databases to their IHP 190 that may be used in interactions between the user's IHP and the data and analytics system 160, for example through the external interfaces $125_1$-$125_n$ (FIG. 1). The external information and databases may include—e.g. favorite apps 805, data from electronic medical records (EMRs) 810, data from databases about genetic diseases 815 and other disease states that are not covered in the base set of disease states in each user's IHP 190, information and databases related to diagnostic tools 820, information and databases related to assistance with insurance and providers 825, information and databases related to nutrition health 830, information and databases related to behavioral health 835 and related crisis calls 840, etc. As noted, every user is unique with different genomes, physiology, personality, preferences, diseases, medications, etc. The granular, flexible data architecture underlying each IHP means that each user can customize what data and capabilities are available to them based on their unique needs—e.g. someone may have behavioral health issues in which case their IHP and health coach would be put in touch with a vetted Behavioral Health set of capabilities. Similarly, as changes keep occurring in health and care, such as the use of personal genome, metabolome and other—omic data, the flexible data architecture allows the user's IHP to, in near real time, adapt its structure and architecture to accommodate this new data, unlike current EMRs which are brittle and more difficult to change. Because of the underlying data and analytics system data architecture, the platform application 175 can connect to the user's home health monitors, their electronic medical records, and other apps that the user may like—e.g. favorite recipe or jogging apps for the nutrition and/or fitness part of their health program. In this way, the health and care management system 100 becomes a super-integrator or platform of platforms, vetting and curating each new source of data before the data can enter a given user's IHP 190, thus dealing with the garbage in garbage out problem and the explosion of digital health devices of unknown quality, safety and security.]

Each time the user enters new data into a user terminal 105, that data may be sent to the data and analytics system 160, which may read an analyze the data and create a new set of guidance options for the user based on that new data. The guidance options may be displayed in an interactive format with various buttons that may provide additional functionality. for example, if the user clicks on a refine button provided under a piece of guidance, the data and analytics system 160 may produce a set of refinement questions from the literature for the user to answer. If the user clicks on one of any number of acute symptoms, the data and analytics system 160 may produce a set of questions for the user to answer. As mentioned above, periodically or with the presentation of new troubling data, the data and analytics system 160 may send to the user's IHP 190 a set of screening questions about an aspect of one of the user's health goals or care plan in order to identify early, and to prevent the emergence of, new or chronic health issue e.g. early identification and prevention of hypoglycemia, depression, and many others.

Each new acute/chronic care/health issue and the data on that issue may be assessed and analyzed in the context of all of a given individual's health and care data and in the context of the relevant peer reviewed literature. There are several analytical techniques that the data and analytics system 160 uses to carry out this analysis. The important point here is that the data and analytics system 160 does not rely on one modeling or analytical technique as most other systems do—e.g. many systems use treatment algorithms that are static and based on probability, not optimization of matching to an individual's particular circumstances. This data and analytics system 160 doesn't just rely on algorithms. It uses the best technique for the analytical question to be answered. So, since triage, diagnosis, treatment and management suggestions are going to change with the underlying science, the setting and the individual in question, so too should the analytical approaches change.]

Referring again to FIG. 8, the system may include a set of quality and safety guard rails for new data coming into the system from an individual's favorite app to make sure that the new data makes sense and is of high quality—e.g. if a temperature reading says 200 degrees Fahrenheit it will not be accepted. The vetting of data may be done as the new candidate data comes into the data and analytics system 160. The quality and safety guard rails may include range limits for each variable—e.g. the body temperature example above. The range limits may be derived from the peer reviewed literature and/or protocols that the medical community has established for ranges of specific clinical/heath issues.

Figure 9:
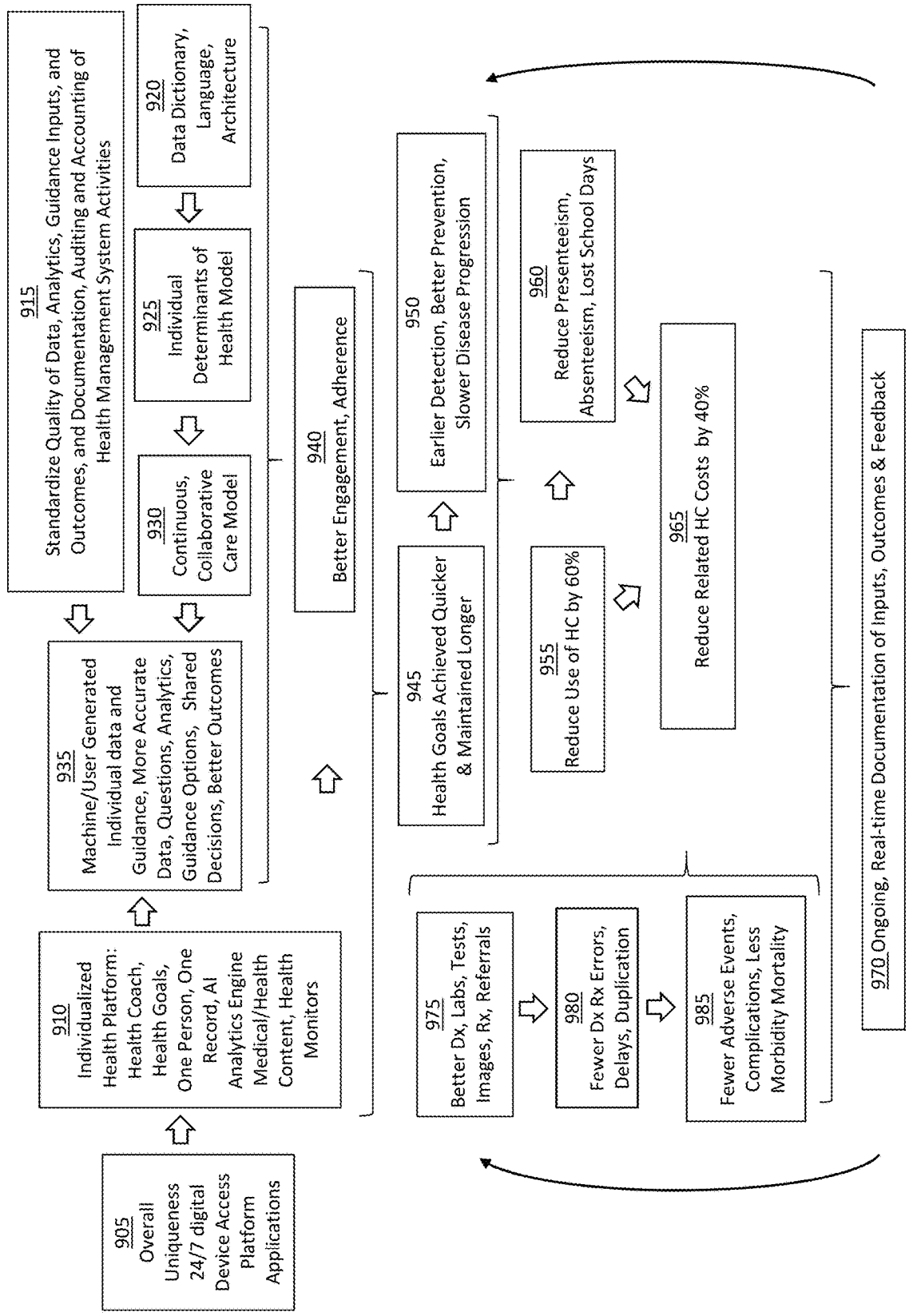
FIG. 9 illustrates various advantages provided by the disclosed health management system.

FIG. 9 illustrates at least some of the advantages provided by the disclosed health and care management system 100:

Overall Uniqueness, Access, and Platform Applications: (Block 905) There are thousands of single shot digital mobile health monitors, wearables and sensors on the market today, but the IHPs 190 are the only 24/7 user terminal device accessible, evidence-based, AI-guided, comprehensive, portable, digital health platforms that bring together and integrate all the resources, including home health monitors, that an individual needs to manage and maximize their own individual health and care, and thus improve their own access, quality, safety, engagement, health, care and cost outcomes. In this way, the IHPs 190 enable each person to become both a provider and consumer of their own health and care efforts—or the new "prosumers" of health and care—chaperoned by the quality and safety guardrails imbedded in the data vetting and contextualized, individual guidance options produced by the data and analytics system 160. Flowing from the nature of the human body, health and care themselves, IHPs are the only integrated, comprehensive health and care platform that enables the drivers and determinants of each person's health to interact with each other in an interdependent manner mirroring the interdependent way the organ systems and other aspects of each person's body interact with each other. IHPs also recognize that each person's particular circumstances of life, family, work, health etc. are unique, and so the tools in each person's IHP need to be taken out to that individual to provide them with the agency they need to find their own path to improved health and care. Every other approach basically asks the individual to come to the clinic, join this or that wellness/disease management program. IHPs take exactly the opposite approach and give the individual the tools they need to fashion their own approach. Each individual may have access to and ownership of their record of their entire health and care history to the extent possible—e.g. one person one record, unlike the current practice of individuals having their data scattered across a number of different electronic medical records (electronic medical records) with a number of different providers.

The system 100 includes platform applications $175_1$-$175_n$ that enable users to access their IHP 190 and a health coach 165 at all times for many different health and care related activities. While most of the day-to-day health and care tasks that a user will want to carry out may be accomplished on relatively smaller devices, such as smartphones, there are some tasks for which larger devices are better suited because of their larger screen sizes. These activities may include the initial collection of the user's health and care data, viewing the full report and background data, references and documentation underlying specific guidance options. The platform applications $175_1$-$175_n$ may operate to adapt the size and amount of information displayed based on the display technology of the user terminal 105, for example, displaying less data with limited data manipulation and reporting on a smaller device while displaying more data with more data manipulation and reporting capabilities on larger devices. Because of the underlying data and analytics system data architecture, the platform application 175 can connect to the user's home health monitors, their electronic medical records, and other apps that the user may like—e.g. favorite recipe or jogging apps for the nutrition and/or fitness part of their health program. In this way, the health management system 100 becomes a super-integrator or platform of platforms, vetting and curating each new source of data before the data can enter a given user's IHP 190, thus dealing with the garbage in garbage out problem and the explosion of digital health devices of unknown quality, safety and security.

Individualized Health Platform: (Block 910) As described in detail above, the—health management system 100 provides an individualized health platform for each user that may include among other things, a health coach, health goals, a one person, one record problem oriented health record model where N=1, an AI analytics engine and health monitors. The IHPs 190 are unique because they are also the only health platforms that mimic the individual, holistic interdependent nature of the human body and thus human health. Each of us has a unique genome, physiology, psychology, living, family and work situation and thus a unique set of health, care, preference and scheduling needs.

Standardize the Quality of the Data, Analytics and Guidance Inputs and Outcomes, and the Documentation, Auditing and Accounting of the Health Management System Activities: (Block 915) The healthcare industry is the only major industry that does not have standards for the quality of the data, analytics and guidance inputs and outcomes, and for the documentation, auditing and accounting of input, outcomes and processes. The health management system 100 has created de facto standards for the industry in lieu of the federal and/or state governments creating these standards, and thus is the only system that has these much— needed standards. Standards for the quality of the data, analytics and guidance inputs and outcomes, and for the documentation, auditing and accounting of system activities: establish de facto standards for the quality of the data, analytics, guidance inputs and outcomes, and for the documentation, auditing and accounting of the health management system 100 activities in taking care of an individual's health and care micro-encounters and needs. As a result, the quality of the initial vetted input data for each health and care issue, and the ongoing collected data is enhanced.

Health/Care Data Dictionary, Language, Ontology and Architecture: (Block 920) The data and analytics system 160 provides a case entity personal health record, an analytics engine and health/medical content development parts of the IHPs 190 and has as its foundation a very flexible, modular, granular health/medical data dictionary, language, ontology and architecture, that makes it possible to establish bi-directional data exchanges between the IHPs 190 and other sources of health/care data such as the external data collection devices 130, electronic medical records, health monitors, etc. provided that the data coming from the sending source of data has standardized, coded data. The data and analytics system 160 vets and curates the data coming from these other data feeds before allowing them to become part of an individual's IHP 190, thus providing the quality and safety guardrails missing from current systems.

Utilization of Individual Determinants: (Block 925) As explained above, the system may operate to collect a list of individual social and environmental health determinants for use in developing the user's health and care plan.

Continuous/Collaborative Care Model, Better Engagement and Management of Chronic Diseases: (Block 930) With 24/7 user terminal device access to their IHPs 190 and the continuous support of their health coaches, users are able to put together realistic health goals and care plans, identify emerging issues earlier, prevent the onset of new chronic diseases, manage their existing chronic diseases more effectively and thus slow down the progression of their chronic diseases from one stage to another. The continuous nature of IHPs also sets them apart because they are able to much more effectively help the user and the health coach set health goals and care plans, work on achieving them on a daily basis by following through on the activities that the guidance options say should be carried out. Currently, with existing systems about 50% of a patient's instructions are ignored and never carried out.

Machine Generated Individual Data and Guidance, More Accurate Data, Questions, Analytics, Guidance Options, Shared Decisions, Better Outcomes: (Block 935) The IHPs 190 are the only systems that have the multiple computerized data collection, data vetting, data refinement and data analytics capabilities to assess each new acute, chronic and/or prevention health/care issue in the context of the rest of that individual's health/care data and in the context of the relevant peer reviewed health/medical literature. No one, including clinicians, can "remember" all this data, carry out this type of multi-factorial analysis and produce individual (not sub-population protocols) guidance options that are free of human cognitive biases, such as confirmation, anchoring and/or many other cognitive biases, which cause many of the medical errors that harm millions of people each year.

By being the only systems that individualize the data inputs and the resulting guidance options, the IHPs 190 are the only systems that, therefore, produce much more precise and accurate data and the foundation for shared decision making between IHP users, their health coaches, primary care physicians and other clinicians on their care team. These better decisions in turn result in far fewer mistakes, adverse events, complications, trips to the ER, hospitals and other clinical settings. All of which may result in a reduction in the use of traditional healthcare services and a drop in associated healthcare costs.

Better Engagement and Adherence—Take Health/Care Resources Out to Each Individual: (Block 940) The IHPs 190 are the only approach that takes this integrated set of health/care resources, out to each person in their own particular circumstances of living, family and work to enable each person with their health coach to figure out what is the best way for them to use these resources and become more involved in their care and health.

Health Goals Achieved More Quickly and Maintained Longer: (Block 945) The system facilitates the user becoming more involved, invested and motivated to achieve their health goals.

Earlier Detection, Better Prevention, Slower Disease Progression: (Block 950) Each user's integrated personal health record 185 may be implemented as an integrated health and care data base that may include all an individual's medical history integrated in one record, that promotes prevention, earlier problem detection, and better disease management that results in slower disease progression.

Better Care, Health and Cost Outcomes: as a result, individual's use of traditional healthcare services may be reduced by approximately 60%, (Block 955), presenteeism and absenteeism may be reduced (Block 960), and related healthcare costs may be reduced by approximately 40%, (Block 965).

Ongoing Documentation, Feedback and Continuous Process Improvement: (Block 970) each IHP 190 tracks, documents, audits and accounts for each click that the individual and/or coach does—e.g. who did what, based on which data, when, why, with what outcomes. This documentation is sent on a continuous basis back up into the AI-driven health, clinical analytics engine for constant learning and process improvement.

Additional system advantages include Better Diagnoses (Dx), Lab Results, Tests, Images, Treatments (Rx), Referrals, (Block 975), Fewer Diagnosis and Treatment Errors, Delays, Duplication, (Block 980), and Fewer Adverse Events, Complications, Less Morbidity Mortality, (Block 985).

The above described components of the health management system 100 work together so that for a given care encounter or health issue, these systems produce the following improvements over current best practices:

Security of User's Health/Care Data: Beyond the encrypted data security protocols that the AWS servers use and that the various components may utilize, the data and analytics system 160 operates to separate a user's personal identifier data from their health/care data. As a result, even if someone were able to hack into a user's account they would not be able to put the personal identifier data together with their health/care data.

Holistic System for Contextualized Health/Care: The human body is also a highly complex system of interdependent biological systems, which means that every new acute, chronic and/or prevention health/care issue that occurs for a given individual needs to be assessed, as the IHPs 190 do, in the context of that individual's entire health/care history, their existing chronic conditions, active acute issues, current medications, vital signs, allergies and other aspects of that person's health/care.

Force Multiplier, Task Shifting, New Division of Labor, Reduce Shortage of Clinicians: The IHPs 190 thus create three new providers, the user, the user's system and the user's health coach. Together, these three new providers can relieve clinicians of all the above data collection, data vetting, data refinement, data analytics and guidance option preparation tasks. These three can also do all the documentation of what happens on each platform—e.g. each click, what happened, with what results, with what inputs, who did it, why, based on which references, etc. In this way, these three new providers represent a new health/care force multiplier at a time when millions of people worldwide are having trouble accessing high quality, safe care and health assistance because of shortages of nurses, primary care physicians and other clinicians.

Relief for Clinicians, Lessons Learned, Continuous Process Improvement and Learning: The above clerical tasks of data collection, etc. are tasks for which clinicians, relative to these three new providers, are ill-suited to perform. We have asked clinicians to do these tasks that are humanly impossible and/or turn highly educated individuals into documentation clerks, which is one of the reasons why clinicians are so dissatisfied with their current situation with resulting high levels of substance abuse, mental illness and suicide. With this new task shifting and division of labor, clinicians are now freed up to focus on more complicated users and on analyzing the outcomes data from the documentation produced by the IHPs 190 for best practices, lessons learned which are fed back up into the AI-analytics engine for continuous process improvement and learning. This continuous provision of best practice data may also reduce legal medical liability and insurance claims.

Higher Quality Refinement of that Data: Better refinement questions on that data, because the questions come from the vetted health/clinical literature not clinicians, who are human and thus have cognitive biases and limited memory capabilities, Higher Quality Analysis of that Data: Better analysis by the AI-driven health/clinical analytics engine of the health/care meaning of the new data in the context of all the other data in that person's health database and in the context of the relevant health/medical literature, Precision Health and Care Guidance Options and Shared Decision Making: More individual, accurate and therefore precise (i.e. precision health and medicine) guidance options and possible next steps for the individual user to discuss with their health coach, primary care physician and other members of their care team for shared decision making, Easier Access and Better Engagement in Health and Care: Because of easier 24/7 access through their smartphone and other digital devices to their IHP 190, the setting of realistic care plans and health goals with their health coach, more ongoing continuous contact with their health coach through sometimes daily nudges, more shared decision making about their care and health issues, individuals become more involved in their care and health, which in turn generates the following three streams of powerful improvements in care, health and cost outcomes:

Better health and care decisions about nutrition, fitness, chronic disease management, diagnoses, labs, images, tests, treatments, acute issues.

Fewer errors, adverse events, complications and trips to the ER, primary care physician or specialists.

Better adherence to care plans and quicker and more sustained achievement of health goals.

Better individual predictive analytics—earlier detection of emerging care and health issues, better prevention of the onset of new issues, and slowing down of progression of existing chronic diseases.

The new division of labor and task shifting produced by the use of the IHPs 190 will produce significant benefits for clinicians or health providers:

They will no longer be required to remember all the user's data and related health and medical literature and try to link the two sets of data to determine guidance options—an impossible task for anyone;

As a result, of not having to perform these tasks, for which they are ill suited relative to the IHPs 190, they will be able to focus their time and attention on tasks for which they are better suited, e.g. spending more time on shared decision making, spending more time on complicated users, spending more time on analyzing the documentation results for process learning and process improvement; and Because the system provides continuous best practice rationale for guidance options, clinicians medical liability risks and insurance premiums will be reduced.

Various modifications and adaptations may become apparent to those skilled in the relevant arts in view of the foregoing description, when read in conjunction with the accompanying drawings. However, all such and similar modifications of the teachings of the disclosed embodiments will still fall within the scope of the disclosed embodiments.

Various features of the different embodiments described herein are interchangeable, one with the other. The various described features, as well as any known equivalents can be mixed and matched to construct additional embodiments and techniques in accordance with the principles of this disclosure.

Furthermore, some of the features of the exemplary embodiments could be used to advantage without the corresponding use of other features. As such, the foregoing description should be considered as merely illustrative of the principles of the disclosed embodiments and not in limitation thereof.

What is claimed is:

1. A method of providing a user with a dynamic, learning, integrated individualized health platform, comprising a system integrating key drivers of an individual's changing health status, the method comprising:

collecting a user's health and care data including socio-economic factors related to family situation, income, employment, type of neighborhood, housing, and education, and personal security issues related to culture, social mores, law and order, and access to police;

using a data and analytics system to organize the collected health and care data into a problem oriented health record for the user comprising records relating to a particular health and care issue arranged as a series of micro care encounters comprising units of measure or analysis relating to the particular health and care issue and organized in order of each step in a diagnostic and treatment and management process in chronological order;

drafting individualized health goals and an individualized care plan specific to the user based on the user's health and care data including the socio-economic factors and personal security issues with the aid of a health coach;

using the data and analytics system to vet and curate the individualized health goals and care plan drafted with the aid of the health coach to assure that the individualized health goals and care plan are supported by applicable peer reviewed best practice health and clinical literature, by:

using a software as a service system to extract bulk data related to individual users from peer reviewed literature, medical monitoring devices, third party applications, and web sites;

using a batch processing system to process bulk data related to individual users available in batch formats, including EHR (Electronic Health Record), CCDA (Consolidated Clinical Document Architecture), and HL7 (Health Level-7) formats;

employing an adapter translator of the data and analytics system to vet, curate, code, time and date stamp the extracted bulk data and the processed bulk data, and associate the vetted, curated, coded, time and date stamped bulk data with the problem oriented health record for the user;

utilizing a lexicon of ontologies of the data and analytics system to store vocabulary and health and care data from vetted published peer-reviewed works;

utilizing a knowledge repository of the data and analytics system to store health and care data extracted from the vetted published works; and utilizing an artificial intelligence (AI) analytics engine of the data and analytics system to:
  review the health data from the adapter translator and review vocabulary and representations stored in the lexicon and knowledge repository to produce and analyze health and clinical analytics and individual health and care knowledge elements to provide updated guidance options in response to the drafted individualized health goals and care plan specific to the user; and
  produce the diagnostic and treatment and management process as comprising individualized guidance options for addressing a user's new acute or chronic issues, managing existing health issues and achieving the health goals and adhering to the care plan based on the user's problem oriented health record, as new coded, vetted, time and date stamped health data coming from one or more of external electronic medical records, remote patient monitoring devices, and wearables is reviewed by the AI analytics engine in real time as input into related guidance options for a current micro care encounter;
the method further comprising:
  providing the individualized health goals and care plan vetted and curated by the data and analytics system to the user's primary care physician for vetting and approval;
  automatically documenting data related to each micro-care encounter, and each activity performed by the user, the health coach, the user's physician, and the data and analytics system for constant learning and process improvement by the data and analytics system;
  storing the individualized health goals and care plan and the documented data in an integrated personal health record of the user;
  monitoring the user's achievements with respect to the individualized health goals and adherence to the individualized care plan;
  identifying a new health and care issue of the user;
  using the data and analytics system to;
    identify a potential problem causing the new heath and care issue and issue a screening survey to identify a condition of the user related to the new health and care issue; and
    use answers to the screening survey to provide additional guidance options based on the peer reviewed literature, related new data from remote patient monitoring devices, the user's social determinants of health and the user's achievements and adherence;
  the method further comprising monitoring the user's achievements with respect to the additional guidance options and storing the additional guidance options and the user's achievements with respect to the additional guidance options in the integrated personal health record.

2. The method of claim 1, wherein collecting the user's health and care data comprises collecting data from one or more electronic medical records, user health monitoring devices and the user's activities on the nutrition and fitness parts of their care plan on a user terminal.

3. The method of claim 1, wherein organizing the collected health and care data into a problem oriented health record comprises organizing the collected health and care data chronologically according to diagnostic, treatment and management guidance, and processes used to address particular medical issues.

4. The method of claim 1, wherein vetting, refining, coding and time and date stamping new data coming into the user's health platform or vetting the health goals and care plan comprises using the data and analytics system to:
  establish standards for quality of the data inputs and the peer reviewed health and clinical literature;
  analyze data from peer reviewed health and clinical literature relevant to a particular micro care encounter and data from the user's remote patient monitoring devices and nutrition and fitness activities to produce health and clinical analytics and the individual health and care knowledge elements to be used in an ongoing manner as inputs into the preparation of new guidance options for addressing new acute and chronic health and care issues; and
  vet the user's health goals and care plan by comparing the health goals and care plan to the data in the peer reviewed best practice health and clinical literature.

5. The method of claim 1, wherein monitoring the user's achievement of the health goals and the user's adherence to the care plan comprises working with the health coach to carryout health activities, including using the patient's remote patient monitoring device, registering on the user's user terminal that the user has carried out nutrition and fitness components of the user's care plan, for achieving the user's health goals and care plan.

6. The method of claim 1, wherein monitoring the user's achievement of the health goals and the user's adherence to the care plan comprises:
  inputting data indicating by the user and the AI analytics engine when a care plan activity is complete; and
  using the data and AI analytics engine to analyze the user's input and behavior against the guidance options, shared decision making and the health goals and care plan.

7. The method of claim 1, wherein providing additional guidance options comprises using the data and AI analytics engine to analyze the user's data inputs in the context of all of the data in the user's problem oriented health record and in the context of the applicable peer reviewed best practice health and clinical literature to produce ongoing guidance options in response to new acute and chronic issues for the user to discuss in shared decision making with the health coach and other members of the user's care team as need be.

8. The method of claim 1, further comprising:
  receiving additional data from the user's remote patient monitoring devices and carrying out and registering on the user's user terminal, the user's daily nutrition and fitness activities as part of the user's care plan; and
  using the data and analytics system to:
    analyze the additional data and identify a potential emerging health problem;
    present the user with one or more of a set of refinement questions about the potential health problem from the best practice peer reviewed literature, or a screening survey for the potential health problem, wherein the screening survey poses refinement and qualifying questions derived from the best practice peer reviewed health and clinical literature applicable to the potential health problem;
    perform an analysis of the user's answers to the refinement questions in the context of the data in the user's problem oriented health record, individual social and environmental health determinants, and in the context of the best practice peer reviewed health and clinical literature related to the new health problem to determine further individualized guidance options for shared decision making between the user, the user's physician, and the user's health coach during one or more interactions.

9. The method of claim 8, further comprising using the further individualized guidance options in shared decision making to plan further health and care steps for resolving the health care problem.

10. The method of claim 9, further comprising storing the individualized guidance options, the health goals and care plan, data related to the user's progress towards the health goals and the user's adherence of the care plan, the additional guidance options resulting from the shared decision making, the further individualized guidance options, and further health and care steps in the user's problem oriented health record.

11. The method of claim 10, wherein the health coach communicates with the user to ensure that the user carries out the health and care activities agreed to as a result of the guidance options and the shared decision making and discussions.

12. The method of claim 1, further comprising providing the user with access to their problem oriented health record at all times.

\* \* \* \* \*